United States Patent [19]

Demmering et al.

[11] Patent Number: 5,773,636
[45] Date of Patent: Jun. 30, 1998

[54] PROCESS FOR THE PRODUCTION OF FATTY ACID LOWER ALKYL ESTERS

[75] Inventors: Guenther Demmering, Solingen; Christian Pelzer, Linnich; Lothar Friesenhagen, Dusseldorf, all of Germany

[73] Assignee: Henkel Kommanditgesellschaft auf Aktien, Duesseldorf, Germany

[21] Appl. No.: 640,921

[22] Filed: Aug. 5, 1996

[30] Foreign Application Priority Data

Nov. 8, 1993 [DE] Germany .......................... 43 38 111.7

[51] Int. Cl.$^6$ .................................................. C11C 1/00
[52] U.S. Cl. ........................................ 554/169; 554/174
[58] Field of Search ..................................... 554/169, 174

[56] References Cited

U.S. PATENT DOCUMENTS

| | | | |
|---|---|---|---|
| 2,177,407 | 10/1939 | Hanley | 260/410 |
| 2,383,579 | 8/1945 | Allen et al. | 260/410.9 |
| 2,727,049 | 12/1955 | Braconier et al. | 260/410.9 |
| 4,608,202 | 8/1986 | Lepper et al. | 260/410.9 R |
| 5,455,370 | 10/1995 | Demmering | 554/169 |

FOREIGN PATENT DOCUMENTS

| | | |
|---|---|---|
| 127104 | 12/1984 | European Pat. Off. . |
| 978993 | 4/1951 | France . |
| 377336 | 8/1932 | United Kingdom . |
| 712747 | 7/1954 | United Kingdom . |
| WO 93/01263 | 1/1993 | WIPO . |

*Primary Examiner*—Gary Geist
*Assistant Examiner*—Deborah D. Carr
*Attorney, Agent, or Firm*—Ernest G. Szoke; Wayne C. Jaeschke; Henry E. Millson, Jr.

[57] ABSTRACT

A process for the production of fatty acid lower alkyl esters comprising the steps of:

A) treating at least one fatty acid ester of glycerol with from about 0.3 to about 3% by weight, based on the weight of ester, of an acid at an elevated temperature;

B) removing said acid from the treated fatty acid ester; and

C) reacting the treated fatty acid ester with at least one lower aliphatic alcohol to transesterify the fatty acid ester.

23 Claims, No Drawings

PROCESS FOR THE PRODUCTION OF FATTY ACID LOWER ALKYL ESTERS

BACKGROUND OF THE INVENTION

This application is a 371 of PCT/EP94/03576 filed Oct. 31, 1994.

1. Field of the Invention

This invention relates to a process for the production of fatty acid lower alkyl esters by transesterification of fatty acid glycerides with lower aliphatic alcohols.

2. Statement of Related Art

Fatty acid methyl esters are important industrial raw materials for the production of a range of products, for example lubricants and surfactants. The esters are normally produced from natural fats and oils, i.e. full esters or partial esters of glycerol with fatty acids, which are transesterified with methanol in the presence of catalysts. Processes relating to the transesterification of fats and oils are described in a number of publications, cf. for example the synoptic article in Seifen-Öle-Fette-Wachse, 114, 595 (1988).

If the transesterification reaction is to be carried out with satisfactory conversions in an economically reasonable time, catalysts have to be added. Suitable catalysts are, in particular, heavy metal compounds such as, for example, zinc oxide (GB 712,747) or zinc silicate (U.S. Pat. No. 2,727,049). Unfortunately, processes such as these are attended by the disadvantage that, after the transesterification, the catalysts cannot remain in the product for toxicological reasons, but instead have to be removed which involves considerable outlay on equipment.

The transesterification reaction may also be carried out in the presence of mineral acids which merely have to be neutralized on termination of the reaction. Although the problem of catalyst removal does not arise in this case, the volume/time yields of transesterification products are distinctly poorer by comparison with heavy metal catalysis which limits the application of the process on an industrial scale. A yield comparable with that obtained with the heavy metal compounds mentioned above is achieved by carrying out the transesterification reaction in the presence of free fatty acids. A corresponding process is disclosed in WO 93/1263 (Henkel).

In the catalytic transesterification processes mentioned above, the natural fatty acid glycerides used as starting compounds have to be treated with bleaching earth ("fullering") in order to remove shell remains and mucins. This pretreatment is necessary to obtain a substantially odorless and light-colored product. After removal of the bleaching earth, the transesterification reaction may be carried out in the presence of the catalysts described above. However, the shell remains and mucins are not completely removed by the treatment with bleaching earth so that the product obtained from the transesterification of fatty acid glycerides with lower aliphatic alcohols is generally attended by an unpleasant odor and is discolored.

Accordingly, the problem addressed by the present invention was to provide an economic process for the transesterification of fatty acid glycerides which would provide a fatty acid lower alkyl ester free from unpleasant odors and discoloration.

DESCRIPTION OF THE INVENTION

The present invention relates to a process for the production of fatty acid lower alkyl esters, in which full and/or partial esters of glycerol with fatty acids corresponding to formula (I):

$$R^1\text{---COOH} \quad (I)$$

in which $R^1$ is an aliphatic hydrocarbon radical containing 5 to 23 carbon atoms and 0 or 1 to 5 double bonds, are reacted with lower aliphatic alcohols containing 1 to 4 carbon atoms at elevated temperature and optionally under elevated pressure, characterized in that, before the transesterification reaction, the full and/or partial esters of glycerol with fatty acids corresponding to formula (I) are treated with 0.3 to 3% by weight, based on the quantity of the full and/or partial esters of glycerol with fatty acids corresponding to formula (I), of an acid at a temperature of 75° C. to 120° C.

It has surprisingly been found that fatty acid glycerides can be transesterified in high yields to form odorless and non-discolored products providing the full and/or partial esters of glycerol with fatty acids used are treated with an acid before the transesterification reaction. This process has the advantage that 1. the shell remains and mucins present in the natural starting products are completely removed so that a white odorless product is obtained and 2. an acid value at which the transesterification reaction can be carried out is established by the treatment with an acid so that there is no need for another catalyst to be added.

Suitable starting materials for the transesterification reaction on which the process according to the invention is based are both full esters and partial esters of glycerol with fatty acids. Triglycerides are preferably used. Typical examples are glycerol esters of caproic acid, caprylic acid, capric acid, lauric acid, myristic acid, palmitic acid, palmitoleic acid, stearic acid, oleic acid, elaidic acid, petroselic acid, linoleic acid, linolenic acid, chaulmoogric acid, ricinoleic acid, arachic acid, gadoleic acid, behenic acid, erucic acid, arachidonic acid and clupanodonic acid.

The glycerol esters of the fatty acids mentioned are natural products, more particularly those in which the glycerol is attached to two or three different fatty acids. Glycerol fatty acid esters based on natural products are fats and oils of animal or vegetable origin, for example coconut oil, palm oil, palm kernel oil, peanut oil, cottonseed oil, rapeseed oil, sunflower oil, coriander oil, linseed oil, soybean oil, beef tallow or fish oil.

According to the invention, the full and/or partial esters of glycerol used are treated before the transesterification reaction with 0.3 to 3% by weight and preferably 0.8 to 1.5% by weight, based on the quantity of the full and/or partial esters of glycerol, of an acid. Suitable acids are $H_2SO_4$, mineral acids and $H_3PO_4$. $H_2SO_4$ is preferably used. The acid treatment is carried out at a temperature of 75° C. to 120° C. and preferably at a temperature of 80° C. to 98° C. The acid is allowed to act on the full and/or partial esters of glycerol used over a period of 3 to 36 hours and preferably over a period of 8 to 16 hours. The acid then has to be completely removed, for example by washing with water, extraction or centrifugation. The acid used should be completely removed to avoid secondary reactions, such as the formation of sulfoesters. The correspondingly treated full and/or partial esters of glycerol with fatty acids corresponding to formula (I) have an acid value of 20 to 70 and preferably in the range from 35 to 70 after the acid treatment and before the transesterification reaction. It is surprising that the transesterification reaction can readily be carried out even at high acid values of up to 70 without being accompanied by any back-reaction into acid and alcohol. There is no need for additional catalysts.

Suitable lower aliphatic alcohols which may be replace the glycerol in the fatty acid ester are ethanol, n-propyl alcohol, i-propyl alcohol, n-butanol or tert.-butanol. The transesterification reaction is preferably carried out with methanol.

The transesterification of the pretreated glycerol ester may be carried out in known manner at elevated temperature and optionally under elevated pressure, for example at temperatures of 150° C. to 300° C. and more particularly at temperatures of 200° C. to 250° C. and under pressures of 1 to 100 bar and preferably under pressures of 50 to 80 bar. The transesterification reaction may be followed by working up in which the glycerol released and residues of unreacted alcohol are removed and the fatty acid lower alkyl ester obtained is distilled or fractionated.

The following Examples are intended to illustrate the invention without limiting it in any way.

EXAMPLES

In a stirred reactor, 320 g (0.5 mole) of unrefined coconut oil with the following fatty acid composition:
Caproic acid: 0.5% by weight
Caprylic acid: 8% by weight
Capric acid: 7% by weight
Lauric acid: 48% by weight
Myristic acid: 17% by weight
Palmitic acid: 9% by weight
Stearic acid: 2% by weight
Oleic acid: 7% by weight
Linoleic acid: 1.5% by weight
Bound glycerol: 13.8% by weight
Acid value: 9.3
were treated with 50% sulfuric acid in a ratio by weight of 99:1 over a period of 24 hours with continuous stirring at 95° C. The sulfuric acid used was removed by extraction. After the treatment with sulfuric acid, the following characteristic data were determined for the coconut oil:
Bound glycerol: 13.1
Acid value: 67

The coconut oil thus pretreated was introduced into a 1 liter autoclave with 320 g (10 moles) of methanol (ratio by volume 1:1). The reaction mixture was then kept at a temperature of 280° C. and under a pressure of 65 bar for 180 minutes. After cooling and venting of the reaction mixture, a transesterification product with the following characteristic data was obtained:
Bound glycerol: 1.1% by weight
Acid value: 2.3.

We claim:

1. A process for the production of fatty acid lower alkyl esters consisting essentially of the steps of:
   A) treating at least one fatty acid ester of glycerol with from about 0.3 to about 3% by weight, based on the weight of ester, of a mineral acid at an elevated temperature;
   B) removing the acid from the treated fatty acid ester; and
   C) reacting the treated fatty acid ester with at least one lower aliphatic alcohol without the use of any added catalyst to transesterify the fatty acid ester.

2. The process of claim 1 wherein following step C) the transesterified ester is isolated from the resulting reaction mixture.

3. The process of claim 1 wherein in step A) the elevated temperature is a temperature in the range of from about 75° to about 120° C.

4. The process of claim 3 wherein said temperature in step A) is in the range of from about 80° to about 98° C.

5. The process of claim 1 wherein in step A) the at least one fatty acid ester of glycerol is an ester of glycerol with at least one fatty acid of the formula:

$$R^1-COOH \qquad (I)$$

wherein $R^1$ is an aliphatic hydrocarbon radical containing from 5 to 23 carbon atoms and from 0 to 5 double; and said ester is selected from the group consisting of full esters, partial esters, and mixtures thereof.

6. The process of claim 1 wherein in step A) from about 0.8 to about 1.5% by weight of acid is used.

7. The process of claim 1 wherein in step A) the treatment time is from about 3 to about 36 hours.

8. The process of claim 7 wherein the treatment time is from about 8 to about 16 hours.

9. The process of claim 1 wherein in step A) the at least one fatty acid ester of glycerol is a natural product based on fats or oils of animal or vegetable origin, or mixtures of the foregoing.

10. The process of claim 1 wherein in step A) the treated ester has an acid value of from about 20 to about 70.

11. The process of claim 10 wherein the acid value is from about 35 to about 70.

12. The process of claim 1 wherein in step B) the residual acid is removed by washing with water, by extraction, or by centrifugation.

13. The process of claim 1 wherein in step C) the at least one lower aliphatic alcohol is at least one of methanol, ethanol, n-propyl alcohol, i-propyl alcohol, n-butanol, and tert.-butanol.

14. The process of claim 13 wherein the at least one lower aliphatic alcohol is methanol.

15. The process of claim 1 wherein step C) is carried out at a temperature of from about 150° C. to about 300° C.

16. The process of claim 15 wherein the temperature in step C) is from about 200° C. to about 250° C.

17. The process of claim 15 wherein in step C) the pressure is from about 1 to about 100 bar.

18. The process of claim 17 wherein the pressure is from about 50 to about 80 bar.

19. The process of claim 5 wherein in step A) the at least one fatty acid ester of glycerol is a triglyceride.

20. A process for the production of fatty acid lower alkyl esters consisting essentially of the steps of:
   A) treating at least one fatty acid ester of glycerol, which is an ester of glycerol with at least one fatty acid of the formula:

$$R^1-COOH \qquad (I)$$

wherein $R^1$ is an aliphatic hydrocarbon radical containing from 5 to 23 carbon atoms and from 0 to 5 double bonds, and said at least one ester is selected from the group consisting of full esters, partial esters, and mixtures thereof, with from about 0.3 to about 3% by weight, based on the weight of ester, of a mineral acid at a temperature in the range of from about 75° to about 120° C.;
   B) removing the mineral acid from the treated fatty acid ester; and
   C) reacting the treated fatty acid ester with at least one lower aliphatic alcohol at a temperature in the range of from about 150° to about 300° C. and a pressure of from about 1 to about 100 bar, wherein step C) is carried out without the addition of any catalyst.

21. The process of claim 20 wherein in step A) the treatment time is from about 3 to about 36 hours, the treated ester has an acid value of from about 20 to about 70; and in step C) the at least one lower aliphatic alcohol is at least one of methanol, ethanol, n-propyl alcohol, i-propyl alcohol, n-butanol, and tert.-butanol.

22. The process of claim 21 wherein in step A) from about 0.8 to about 1.5% by weight of mineral acid is used, the treatment temperature is in the range of from about 80° to about 98° C., the pressure is from about 50 to about 80 bar, and the treated ester has an acid value of from about 35 to about 70; and the temperature is step C) is from about 200° C. to about 250° C.

23. The process of claim 21 wherein in step A) the at least one fatty acid ester of glycerol is a natural product based on fats or oils of animal or vegetable origin, or mixtures of the foregoing.

* * * * *